United States Patent
Brard et al.

(10) Patent No.: US 8,252,780 B2
(45) Date of Patent: Aug. 28, 2012

(54) ORGANOMETALLIC COMPLEXES AS THERAPEUTIC AGENTS

(75) Inventors: Laurent Brard, Skekonk, MA (US); Rakesh Singh, Barrington, RI (US); Satyan Kalkunte, Providence, RI (US); Robert Strongin, Baton Rouge, LA (US); Onur Alpturk, Baton Rouge, LA (US)

(73) Assignees: Women & Infants' Hospital, Providence, RI (US); Louisiana State University, Baton Rouge, LA (US)

( * ) Notice: Subject to any disclaimer, the term of this patent is extended or adjusted under 35 U.S.C. 154(b) by 140 days.

(21) Appl. No.: 12/516,878

(22) PCT Filed: Nov. 30, 2007

(86) PCT No.: PCT/US2007/086080
§ 371 (c)(1), (2), (4) Date: Jun. 22, 2010

(87) PCT Pub. No.: WO2008/070557
PCT Pub. Date: Jun. 12, 2008

(65) Prior Publication Data
US 2010/0273763 A1 Oct. 28, 2010

Related U.S. Application Data

(60) Provisional application No. 60/872,249, filed on Dec. 1, 2006.

(51) Int. Cl.
*A61K 31/555* (2006.01)
*A61K 31/295* (2006.01)
*A61P 35/00* (2006.01)
*C07D 271/04* (2006.01)
*C07D 209/34* (2006.01)
*C07D 333/36* (2006.01)
*C07F 15/02* (2006.01)

(52) U.S. Cl. ........ 514/186; 514/185; 514/502; 548/106; 548/403; 549/3; 556/32

(58) Field of Classification Search .............. None
See application file for complete search history.

(56) References Cited

U.S. PATENT DOCUMENTS

| | | | |
|---|---|---|---|
| 4,798,824 | A | 1/1989 | Belzer et al. |
| 4,873,230 | A | 10/1989 | Belzer et al. |
| 4,879,283 | A | 11/1989 | Belzer et al. |
| 5,145,771 | A | 9/1992 | Lemasters et al. |
| 5,403,834 | A | 4/1995 | Malfroy-Camine et al. |
| 5,629,008 | A | 5/1997 | Lee |
| 5,696,109 | A | 12/1997 | Malfroy-Camine et al. |
| 5,827,880 | A | 10/1998 | Malfroy-Camine et al. |
| 5,834,509 | A | 11/1998 | Malfroy-Camine et al. |
| 5,851,547 | A | 12/1998 | Fujioka et al. |
| 6,183,461 | B1 | 2/2001 | Matsuura et al. |
| 6,589,948 | B1 | 7/2003 | Malfroy-Camine et al. |

FOREIGN PATENT DOCUMENTS

WO WO9114672 10/1991

OTHER PUBLICATIONS

Watanabe et al., Chemical Communications (2006), vol. 47, p. 4958-4960.*
Reddinger et al. Macromolecules, (1997), vol. 30, p. 673-675.*
International Search Report dated May 5, 2008 of corresponding PCT Application No. PCT/US07/86080.

* cited by examiner

*Primary Examiner* — Yong Chu
(74) *Attorney, Agent, or Firm* — Rissman Hendricks & Oliverio LLP

(57) ABSTRACT

This invention comprises salophene-based metallic complexes. Included are metal-chelating analogues, and method of their preparation and use. These analogues have therapeutic activity including anticancer activity.

4 Claims, 7 Drawing Sheets

The Mass spectrum of methyl-dioxyphenyl-salophene.

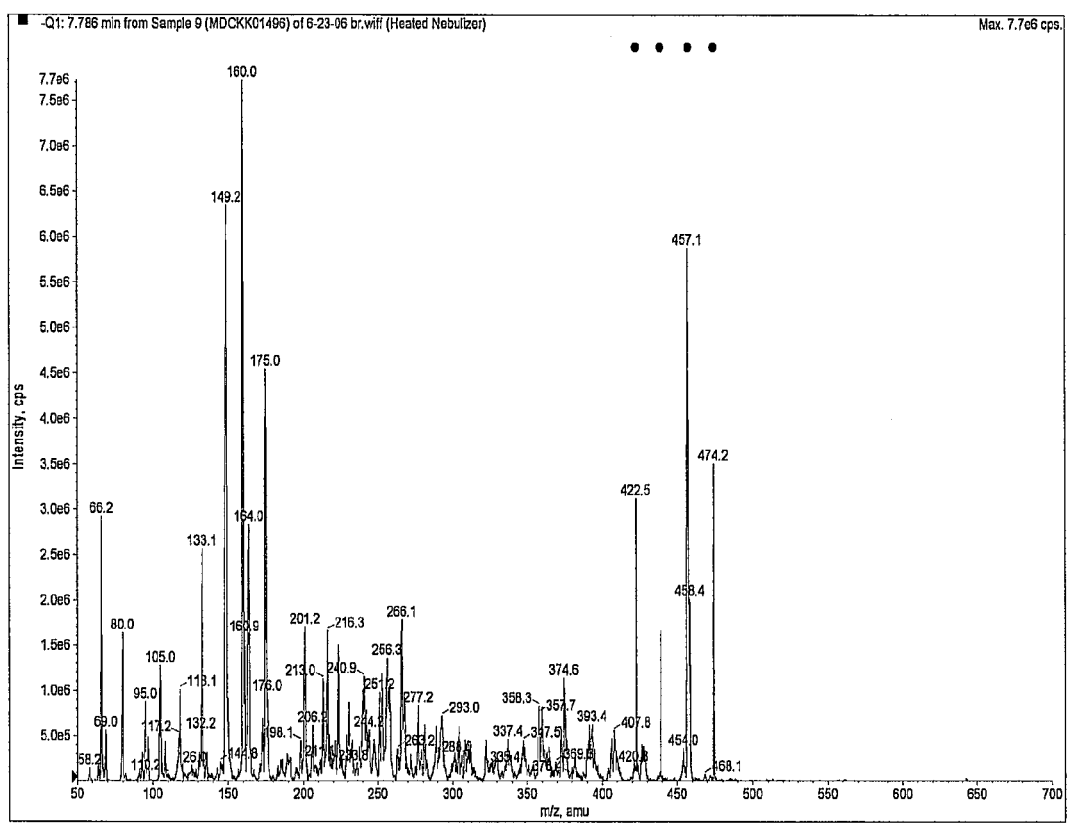
Fig. 6. The mass spectrum of Furazone-metallosalophene.

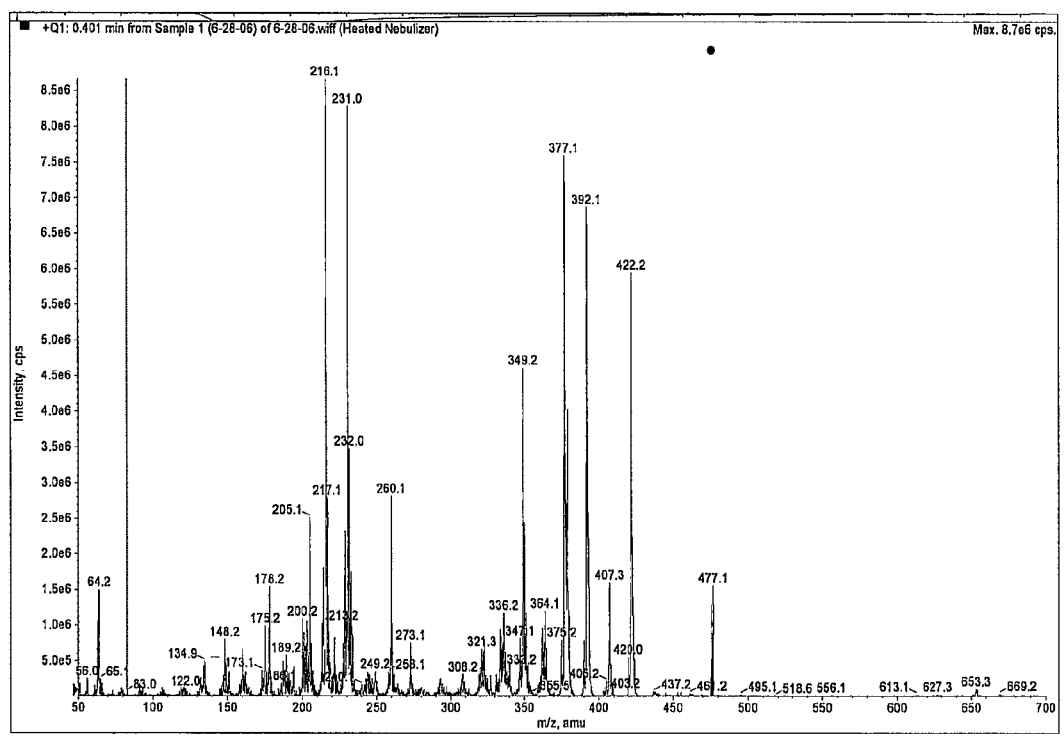
Fig. 7. The mass spectrum of the Furazone-metallosalophene in APCI mode.

ORGANOMETALLIC COMPLEXES AS THERAPEUTIC AGENTS

CROSS REFERENCES TO RELATED APPLICATIONS

This application is a national phase application of, and claims priority to, PCT/CA2007/086,080, filed on Nov. 30, 2007, which claims the benefit of priority under 35 U.S.C. §119(e) to U.S. patent application Ser. No. 60/872,249 filed on Dec. 1, 2006, the disclosures of which are incorporated herein by reference.

FIELD OF THE INVENTION

This invention comprises of the synthesis, biological evaluations and applications and pharmaceutical compositions of synthetic organometallic complexes herein called Metallosalophenes (MSP). Included are metal-chelating analogues, and method of their preparation and use.

Further the invention comprises of methods of use of MSPs for targeted protection of tissues and/or cell types during cancer chemotherapy, as de-novo drugs and or analogues possessing such therapeutic applications as antineoplastic, anti-angiogenic and anticancer activity and others such as free radical scavenging and the other diseases born out of it and others such as anti-Alzheimer's.

In addition, this invention provides compositions and methods that are useful for chemoprevention of chemical carcinogenesis and alterations of drug metabolism involving the epoxides or free oxygen radicals or intermediates. Such a potential is indicated in the usefulness of these classes of compounds for preventing the oxidative damage in human transplant organs and for inhibiting reoxygenation injury following the reperfusion of ischemic tissues.

Other important aspects of invention relate to their potential to act as chemical sensors for the detection of bio-chemicals such as saccharides and sugars, glycolipids and phospholipids.

BACKGROUND OF THE INVENTION

The complexation of neutral molecules has become a rapidly growing field since the work of Pedersdon (Pederson et al *J. Am Chem. Soc* 1967, 89, 2495 and *J. Org. Chem* 1971, 36, 1690) on synthetic host molecules. Related complexes have been found to possess synthetic chemistry applications (see, Fu et al *J. Org. Chem.* 1991, 56, 6497; Zhang W and Jacobson E. N. 1991, 56, 2296; Jacobson et al *J. Am Chem. Soc* 1991, 113, 6703; Zhang et al *J. Am Chem. Soc* 1990, 112, 2801; Lee N. H. and Jacobson et al *Tetrahedron lett* 1991, 32, 6533; Jacobson et al *J. Am. Chem. Soc* 1991, 113, 7063; Lee et al *Tetrahedron lett* 1991, 32, 5055. These, and all publications cited herein, are incorporated by reference.

Malfroy-Camine et al. (U.S. Pat. No. 6,589,948 B1) has disclosed metal complexes useful as potent anti-oxidants. Other uses are disclosed in the U.S. Pat. Nos. 5,403,834; 5,834,509; 5,696,109 and 5,827,880.

BRIEF DESCRIPTION OF THE INVENTION

It has now been discovered that a number of MSPs display anticancer activity. This has been demonstrated in vitro in various cultured solid tumor cancer cells such as neuroblastoma, breast, ovarian, prostate, pancreatic, vulvar, and liver and in other non-solid human tumors too. Furthermore, MSP anticancer activity is present in vivo.

This invention includes compounds having the formula (I) or (II):

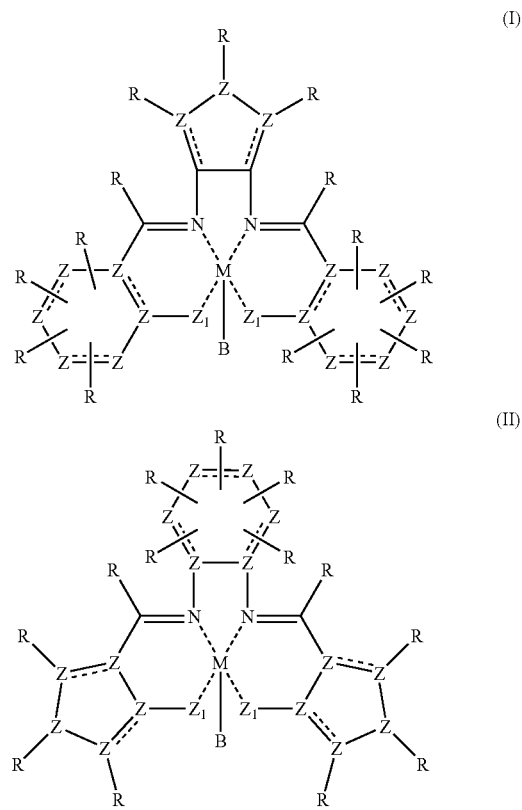

wherein

B is selected from ligands such as halides, acetate, oxalates, succinate, fumarates, tartarates.

Z is selected from the group consisting of C, N, O or S;

R is selected from the group consisting of H, amino, hydroxyl, halogens, alkyl, aryl, heteroaryl, arylalkyl, acetyl, carbamates, urea, or thiourea, alkyl, alkenyl, alkynyl, aryl, heteroaryl, arylalkyl, heteroarylalkyl, OH, COOH, CHO, halide, $NO_2$, or $NH_2$, or said substituent further combined with at least one substituent selected from the group consisting of amide, urea, thiourea, CN, bicyclic amine, or bicyclicdiamine;

M is a metal;

$Z_1$ is selected from the group consisting of O, N or S.

This invention further comprises a compound I of claim 1 having the following structure

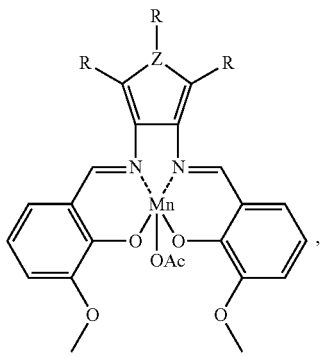

wherein Z is selected from the group consisting of C, N, O or S; and,

R is selected from the group consisting of H, amino, hydroxyl, halogens, alkyl, aryl, heteroaryl, arylalkyl, acetyl, carbamates, urea, or thiourea, alkyl, alkenyl, alkynyl, aryl, heteroaryl, arylalkyl, heteroarylalkyl, OH, COOH, CHO, halide, $NO_2$, or $NH_2$, or said substituent further combined with at least one substituent selected from the group consisting of amide, urea, thiourea, CN, bicyclic amine, or bicyclicdiamine.

In a particular embodiment this invention includes compounds I and II wherein one or more R substituents is further combined to form a substituent selected from the group consisting of piperazine, piperidine, peptidic bonds, alkyl, aryl, arylalkyl, fused saturated, half saturated two or four cyclic or heterocyclic rings or sugar, and optionally wherein M is a transitional metal, and further optionally wherein in transitional metal is selected from the group consisting of lanthanides or actinides, with particular reference to rhodium, lanthanum, and iron.

In a specific embodiment this invention is drawn to a compound of the following structure

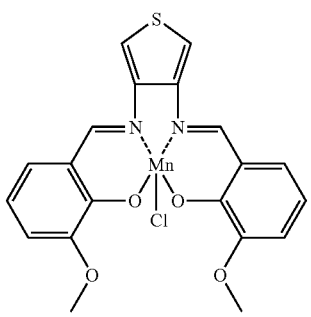

This invention further includes methods of treating a subject in need of such treatment by administering to such subject a therapeutically effective dose of a compound of the following structure:

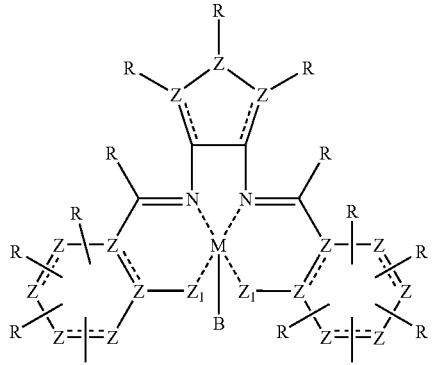

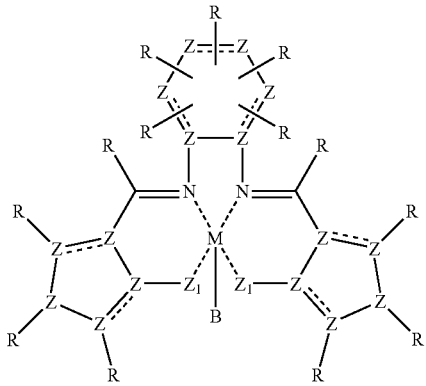

This method specifically contemplates treatment of cancer including ovarian, breast and cervical cancer. Particular dosages include from about 5 mg to about 5 g. In some regiments, dosages are about 0.01 to 1000 milligram (mg) per kilogram (kg) of body weight of recipient per day, and about 1 to 100 mg per kg of body weight of recipient per day. Particular reference is made to dosage of about 2 to 20 mg per kg of body weight of recipient per day.

BRIEF DESCRIPTION OF THE DRAWINGS

FIG. 6. The mass spectrum of Furazone-metallosalophene.

FIG. 7. The mass spectrum of the Furazone-metallosalophene in APCI mode.

V. DETAILED DESCRIPTION OF THE INVENTION

Figure 1:
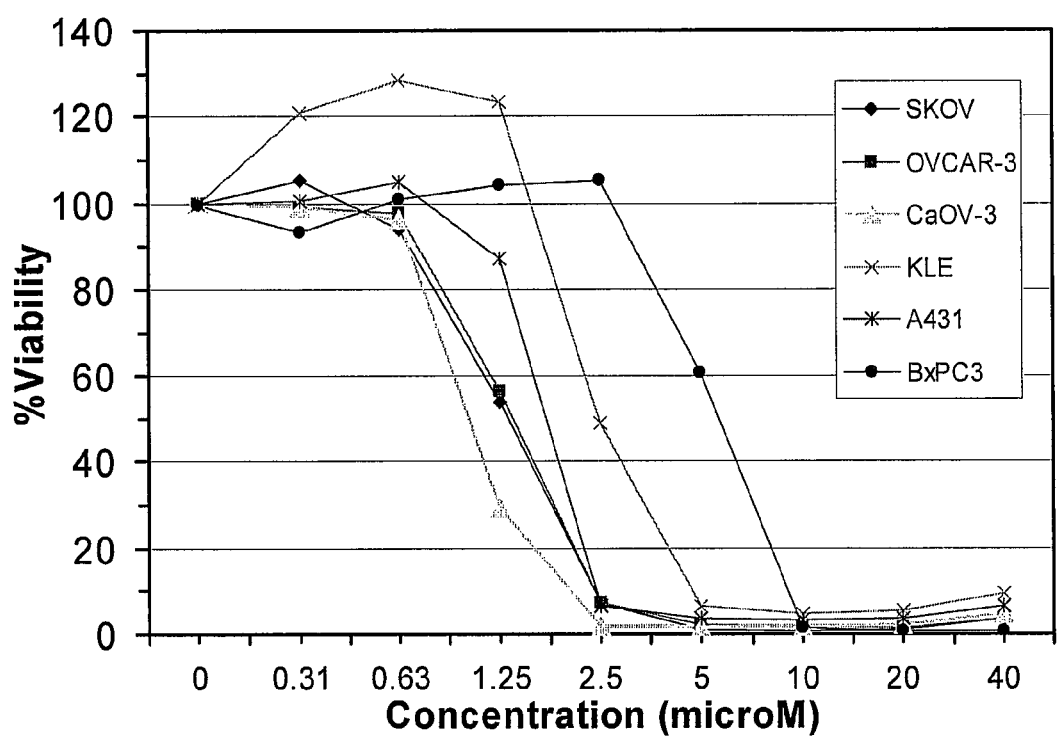
FIG. 1. Graph of the cytotoxic activity of Metallosalophene complexes in A431 (epidermoid), BxPC3 (pancreatic cancer), KLE (endometrial cancer), Ovcar-3, CaOv-3, SKOV-3 (ovarian cancer) cell lines.
Figure 2:
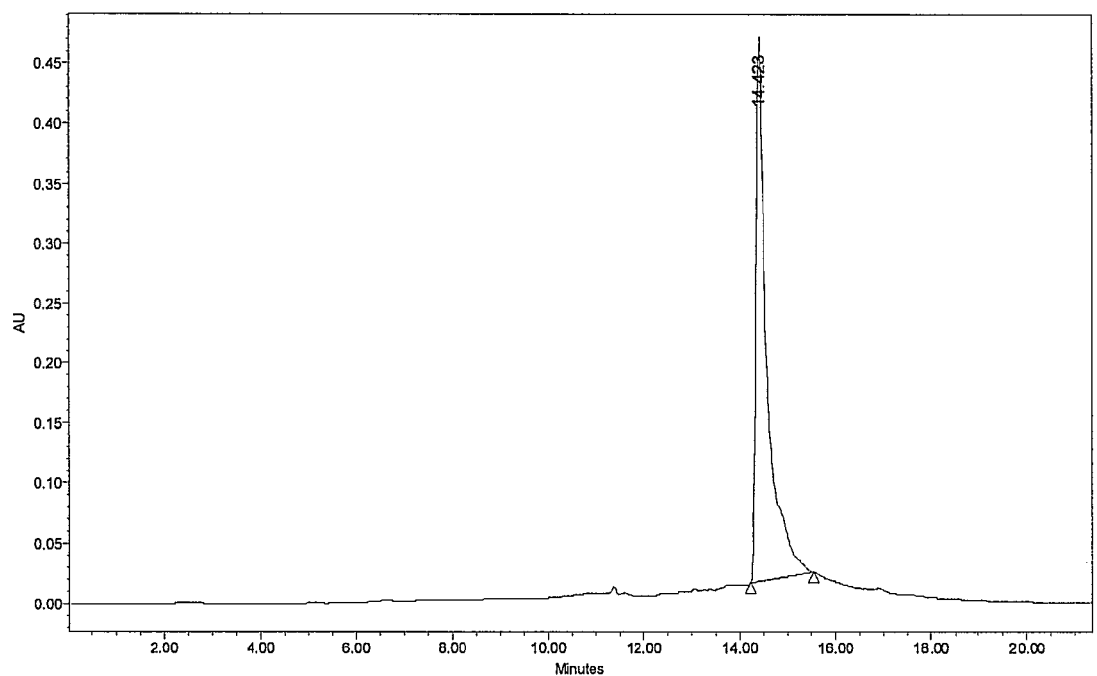
FIG. 2. The HPLC chromatogram of the methylene-dioxyphenyl-metallosalophene.
Figure 3:
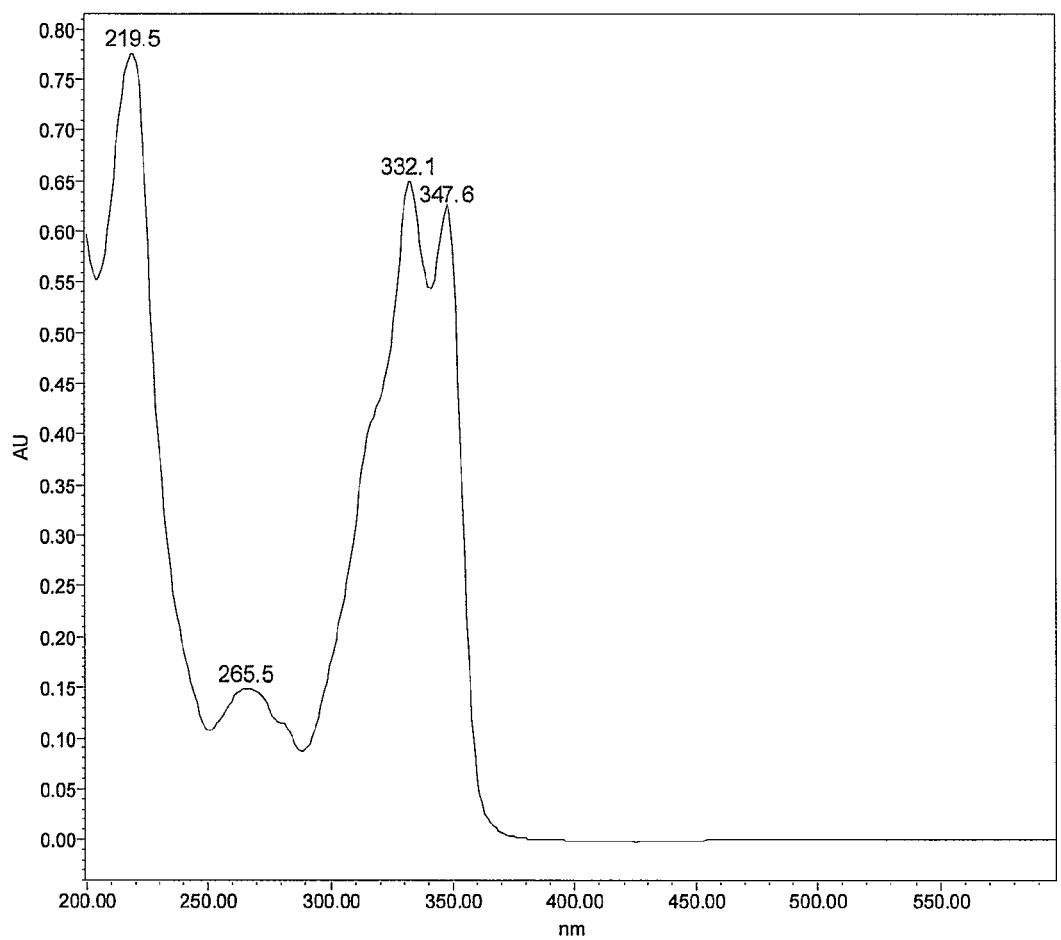
FIG. 3. The ultra-violet spectrum of the methylene-dioxyphenyl-metallosalophene.
Figure 4:
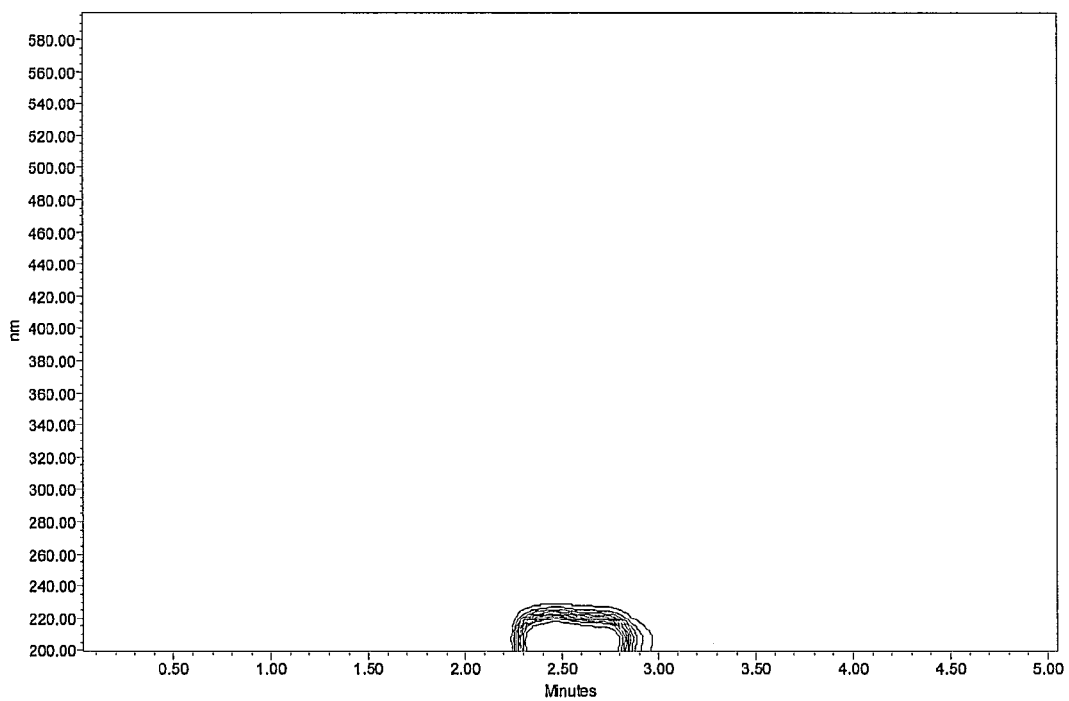
FIG. 4: A PDA-view of the methylene-dioxyphenyl-metallosalophene.
Figure 5:
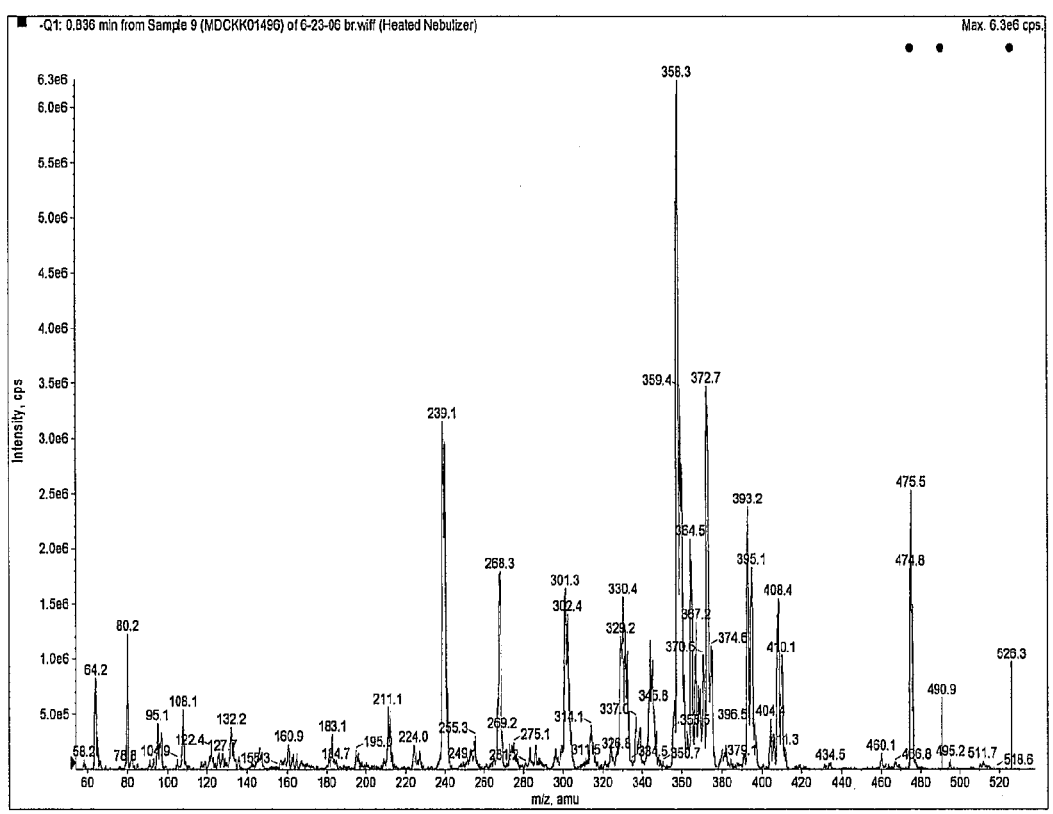
FIG. 5 The Mass spectrum of methylene-dioxyphenyl-salophene.

The instant invention will be better understood with reference to the following definitions:

A. The term "Alkyl" shall mean one or more linked carbon atoms such as (C)n such that "n" is any number of carbons in a chain. Contemplated chains include linear, branched or cyclic chains including alkene, alkenyl, alkynyl, with particular mention of carbon chains where n=2-20. This term is exemplified by groups such as methyl, ethyl, n-propyl, n-butyl, iso-butyl, tert-butyl, n-hexyl and n-decyl, tetradecyl and the like.

"Substituted/substituents" is used in conjunction with alkyl. Substituents(s) can be pendent from the alkyl group, interrupt the alkyl group, or both pendent from, and interrupting the alkyl group. Substituted alkyl moieties are also contemplated within the definition of alkyl. Substituted alkyls include, for example, alkenyl, alkynyl, alkoxy, cycloalkoxy, cycloalkenyl, acyl, acylamino, acyloxy, alkoxycarbonylamino, azido, cyano, halogen, hydroxyl, oxo, thiocarbonyl, carboxy, arythio, thiol, alkylthio, aryloxy, aralkoxy, heteroaryloxy, aminosulphonyl, COOR where R is hydrogen, alkyl, aryl, aryl alkyl, NHC(=O)R$_1$x, NR$_1$xR$_1$x, —NHC(=O)NR$_1$xR$_1$x, C(=O)aryl, C(=O)heteroaryl, C(=O)heterocyclylalkyaryl, C(=O)alkyl, —OC(=O)NR$_1$xR$_1$x, [where R$_1$ is independently hydrogen, alkyl, aryl, aryl alkyl and x is independently integers 1-2], nitro, S(O)R$_1$x. It is further contemplated that additional substituents may be constructed onto the basic organometallic complex with equivalent or improved activity.

B. The term "aryl" means $C_4$ to $C_{12}$ aromatic or heteroaromatic ring systems which further include ring substitution with alkyl groups and other functional groups such as —OH and derivatives thereof such as ethers, and acetates, NRR and derivatives thereof, such as amides, thioamides, ureas, thioureas, carbamates, thiocarbamates etc, SH and derivatives thereof such as thioethers, and COOH and derivatives thereof such as esters, amides.

Particular reference is made to the substitutions of the groups described above with following class of groups such as amino acids (optically active, including antipodes, racemic, and synthetic/unnatural amino acids), peptides (open or cyclic) containing all coded and uncoded amino acids (as described in literature) in single or in multiple repeating units such as polypeptides. Sugars and other class of molecules which may be categorized as biologicals and other natural products such as hormones, vitamins etc.

Some of the moieties described below represent the body of the broad scope of the present invention.

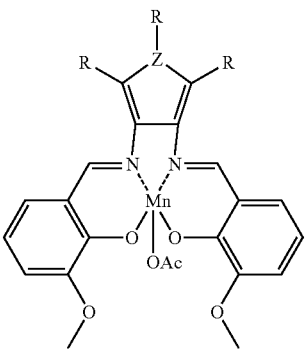

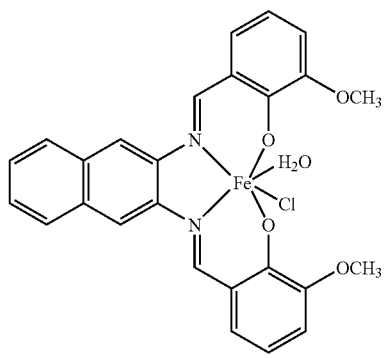

Naphthyl-iron salophene

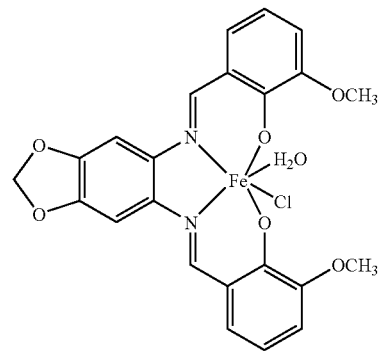

Methylene-dioxyphenyl-iron salophene

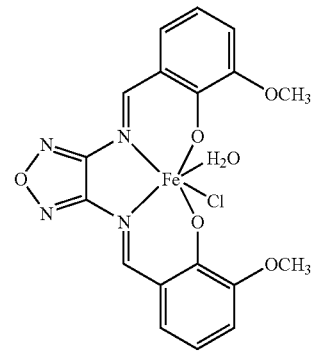

Furazone-iron salen

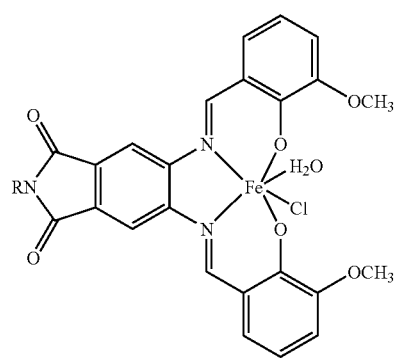

Phthalimide-iron salophene (R = H)

Where:

Z is selected from S, N, O and C and $Z_1$ is selected from S, N, and O.

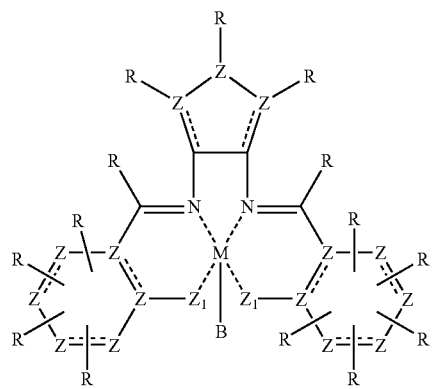
(I)

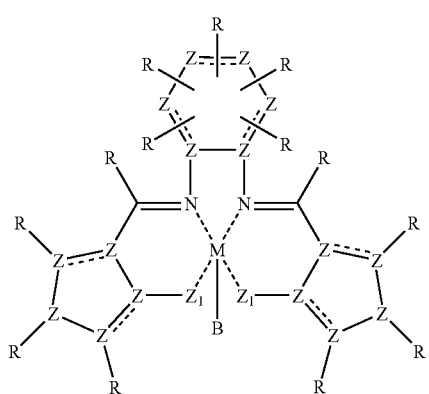
(II)

C. B is selected from ligands such as halides, acetate, oxalates, succinate, fumarates, tartarates.

D. M refers to the metals, preferably the transition metal, lanthanides, actinides. Metals useful in the composition of this invention include transitional metals such as well as Fe, Ni, Cu, Mn, Co, Mg. Transitional metals are elements from the B group of the periodic table. Transition metals have partially filled d sublevels. Specific reference is made to Ag, Au, Sc, Yb, La, Ac, B, Al, Ga, In and Tl.

E. The term "alkylarene" is used herein to refer to a subset of "aryl" in which the aryl group is substituted with an alkyl group.

F. The term "acyl" is used to describe a ketone substituent, —C(O)R, wherein R is alkyl or substituted alkyl, aryl or substituted aryl.

G. The term "alkoxy" is used herein to refer to the —OR group, wherein R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, and t-butoxy.

H. The term "aryloxy" refers to a group having the structure —O—Ar, where Ar is an aromatic group. Particular attention is drawn to the aryloxy group phenoxy.

I. The term "alkylamino" denotes secondary and tertiary amines wherein the alkyl groups may be either the same or different and may consist of straight or branched, saturated or unsaturated hydrocarbons.

J. The term "unsaturated cyclic hydrocarbon" is used to describe a non-aromatic group with at least one double bond, such as cyclopentene, cyclohexene, and substituted analogues thereof.

K. The term "heteroaryl" as used herein refers to aromatic rings in which one or more carbon atoms of the aromatic ring(s) are substituted by a heteroatom such as nitrogen, oxygen or sulfur. Heteroaryl structures may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, or benzo-fused analogues of these rings are included in the term "heteroaryl."

"Substituted heteroaryl refers to heteroaryl as just described wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are encompassed by the term "substituted heteroaryl."

L. "Alkylheteroaryl" defines a subset of "heteroaryl" substituted with an alkyl group M. The term "heterocyclic" is used herein to describe a saturated or unsaturated non-aromatic group having a single ring or multiple condensed rings from 1-12 carbon atoms and from 1-4 heteroatoms selected from nitrogen, sulfur or oxygen within the ring. Such heterocycles are, for example, tetrahydrofuran, morpholine, piperidine, pyrrolidine, etc.

N. The term "substituted heterocyclic" as used herein describes a subset of "heterocyclic" wherein the heterocycle nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

O. The term "alkylheterocyclyl" defines a subset of "heterocyclic" substituted with an alkyl group, as defined herein.

P. The term "substituted heterocyclicalkyl" defines a subset of "heterocyclicalkyl" wherein the heterocyclic nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

Q. The term "fatty acid ester," as used herein, refers to a substituent that is derived from a fatty acid by removal of a hydrogen. When present, the fatty acid esters typically occupy no more than two substituent positions and are usually identical.

A number of compounds of this invention were synthesized and screened for biological activity.

Thiophene-salophenes were synthesized as per the scheme described below.
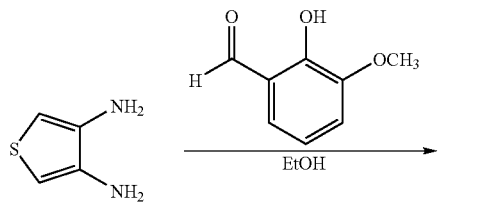
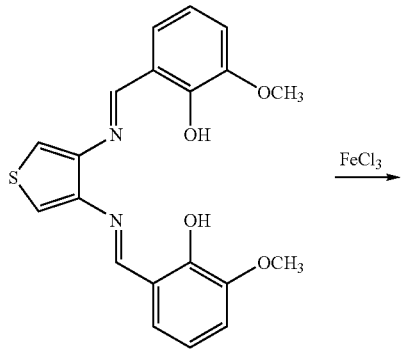
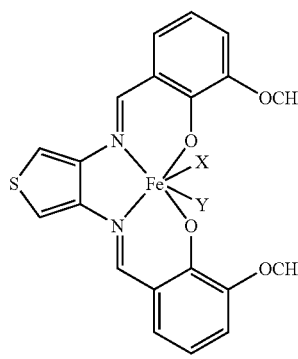
Naphthyl-salophenes were synthesized as per the scheme described below
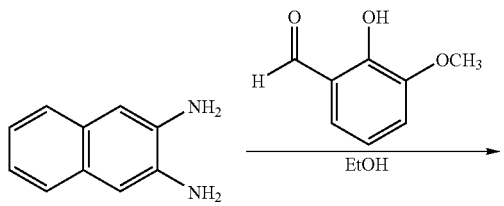
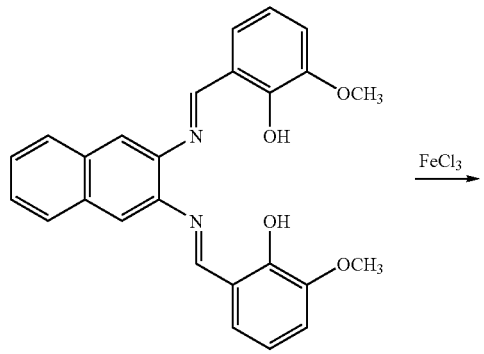
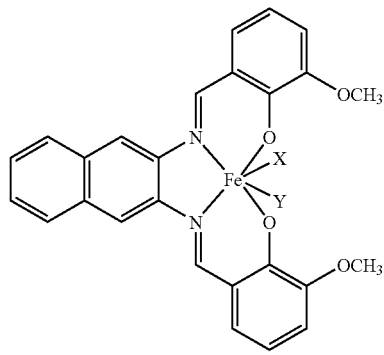
Another class of compounds can be synthesized by the scheme described below
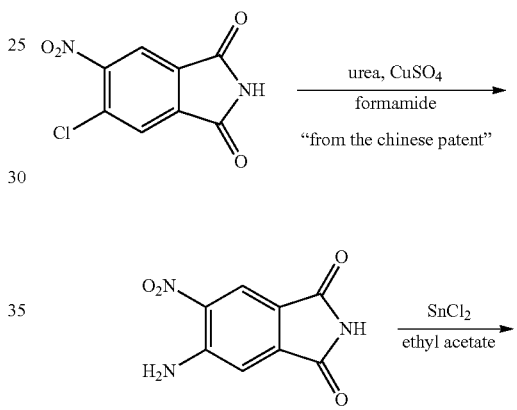
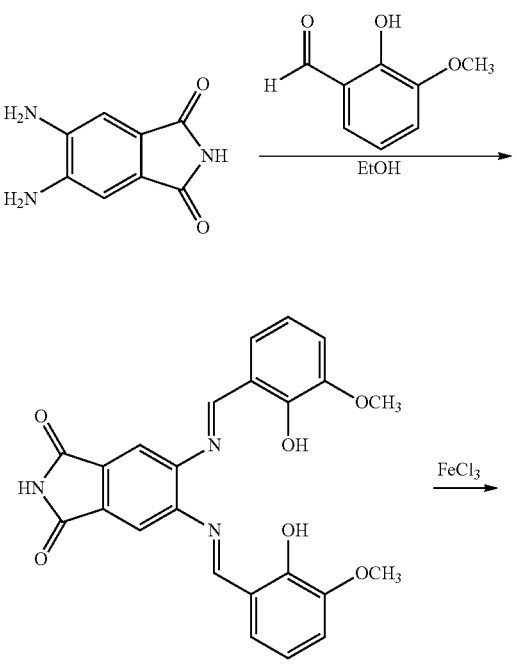

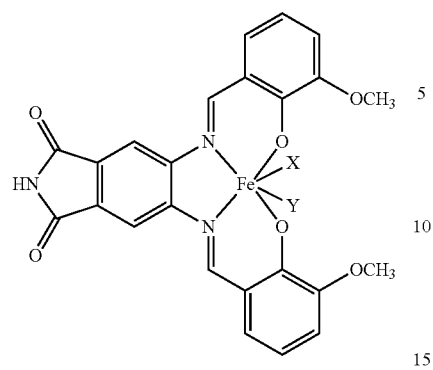
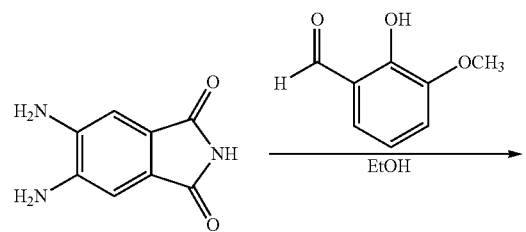
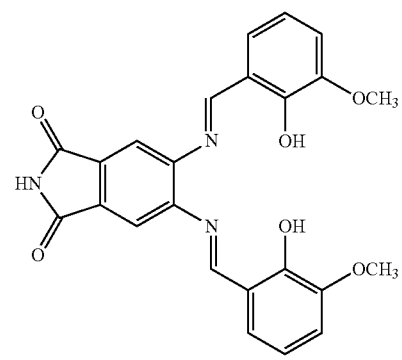
This class of compounds can also be synthesized using the following protocol.
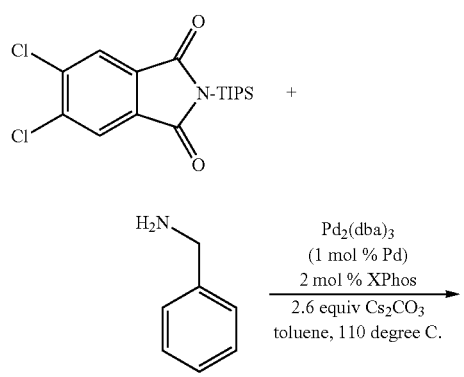
Hennessy, E. J.; Buchwald, S. L. *J. Org. Chem.*, 2005, 70, 7371-7375
Furazone-metallosalophenes were synthesized by following the scheme:
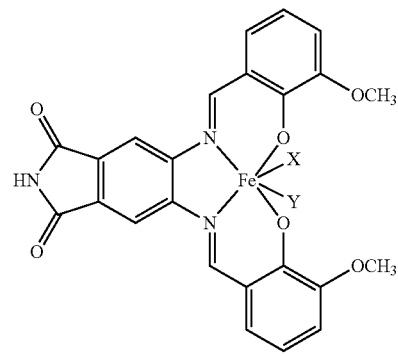
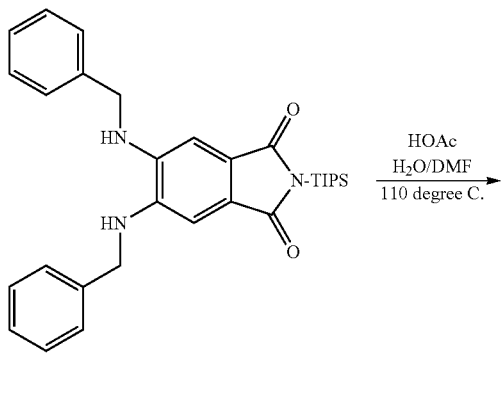
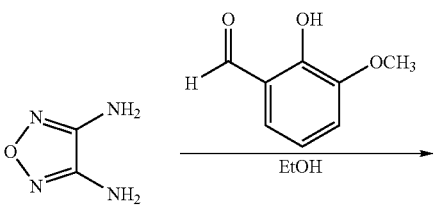
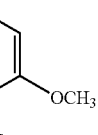

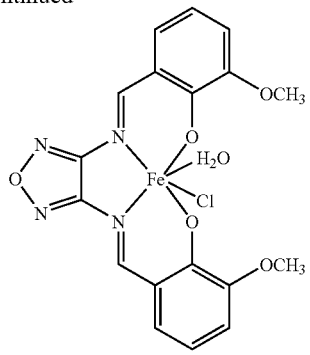

whereas methylene-dioxy metallosalophene were synthesized by the protocol noted below In particular embodiments, preparation of salophene-based metal complexes is performed essentially as described in US91/01915 filed 21 Mar. 1991, Fu et al. (1991) J. Org. Chem. 56: 6497; Zhang W and Jacobsen E N (1991) J. Org. Chem. 56: 2296; Jacobsen et al. (1991) J. Am. Chem. Soc. 113: 6703; Zhang et al. (1990) J. Am. Chem. Soc. 112: 2801; Lee N H and Jacobsen E N (1991) Tetrahedron Lett. 32: 6533; Jacobsen et al. (1991) J. Am. Chem. Soc. 113: 7063; Lee et al. (1991) Tetrahedron Lett. 32: 5055 each of which is incorporated herein by reference.

A particular preparation of the salophene-based metal complex of the present invention is a condensation reaction with the substituted salicylaldehyde and the substituted diamine. In general, quantities of these compounds are reacted in a 2 to 1 molar ratio in absolute ethanol. The solutions are refluxed typically for 1 hour, and the salophene ligand is either precipitated in analytically pure form by addition of water, or the metal complex is generated directly by addition of the metal as its acetate, halide, or triflate salt.

The salophene ligand is redissolved in hot absolute ethanol to give a 0.1 M solution. Solid $Mn(OAC)_2 \cdot 4H_2O$ (2.0 equivalents) is added in one portion and the solution is refluxed for 1 h. Approximately 3 equivalents of solid LiCl are then added and the mixture is heated to reflux for an additional 0.5 h. Cooling the mixture to 0° C. affords the Mn(III) complex as dark brown crystals which are washed thoroughly with $H_2O$ and isolated by filtration in approximately 75% yield. An additional crop of material can be obtained by dropwise addition of $H_2O$ to the mother liquor. Combined yields of catalyst are typically about 80-95% for this step, and about at least 80-90% overall from the optically pure 1,2-diphenylethylene diamine.

Another method of preparing the complexes is as follows: The starting diamine is R,R- or S,S-1,2-diamino-1,2-diphenylethane and the starting salicylaldehyde is 3-tert-butylsalicylaldehyde. A solution of 2.0 mmol of 3-tert-butylsalicylaldehyde in 3 ml of absolute ethanol is added dropwise to a solution of 1.0 mmol of (R,R)-1,2-diamino-1,2-diphenylethane in 5 ml of ethanol. The reaction mixture is heated to reflux for 1 h and then 1.0 mmol of $Mn(OAC)_2 \cdot 4H_2O$ is added in one portion to the hot (60° C.) solution. The color of the solution immediately turns from yellow to brown upon addition. It is refluxed for an additional 30 min and then cooled to room temperature. A solution of 10% NaCl (5 ml) is then added dropwise and the mixture stirred for 0.5 h. The solvents are then removed in vacuo and the residue is triturated with 50 ml of $CH_2$—$C_{12}$ and 50 ml of $H_2O$. The organic layer is separated and the brown solution is washed with saturated NaCl. Separation of the organic phase and removal of solvent resulted in a crude material which can be recrystallized from $C_6H_6/C_6H_{14}$ to give a (R,R)-salophene-Mn complex.

According to this invention, a therapeutically or pharmaceutically effective amount of a salophene-based metallic complex is administered to a patient to treat or prevent neoplastic disease with particular reference to cancer. In particular embodiments the salophene-based metallic complex of this invention is used to therapeutically treat neuroblastoma, pancreatic, ovarian, prostate, endometrial, cervical and colorectal cancers as well as lymphoma, leukemia.

The required dosage will depend upon the nature of the disease, the severity and course of the disease, previous therapy, the patient's health status and response to the salophene-based metallic complex, and the judgment of the treating medical care giver. Typically, at least one species of salophene-based metallic complex is administered as the sole active ingredient, or in combination with one or more other active ingredients, typically selected from the group consisting of: N-2-mercaptopropionylglycine, N-acetylcysteine, glutathione, dimethyl thiourea, desferrioxamine, mannitol, .alpha.-tocopherol, ascorbate, allopurinol, 21-aminosteroids, calpain inhibitors, glutamate receptor antagonists, tissue plasminogen activator, streptokinase, urokinase, nonsteroidal anti-inflammatory agent, cortisone, and carotenoids. salophene-based metallic complex may also be administered in conjunction with polypeptides having SOD and/or catalase activity.

The present invention includes a method of treating patients, such as humans, who have a neoplasticity associated disease with a prophylactically effective or therapeutically effective amount of a salophene-based metallic complex. This method can be used to treat patients at various stages of their diseases or to prevent development of such diseases in patients. In addition, the treatment can be administered to prevent or reduce, as a prophylactic, the age-adjusted probability of developing a neoplasm and/or the age-adjusted mortality rate and/or the rate of senescence.

The salophene-based metallic complexes of the invention can also be administered to patients who are infected with a human immunodeficiency virus (e.g., HIV-1) or who are at risk of becoming infected with a human immunodeficiency virus.

The salophene-based metallic complexes prevent or inhibit the induction of HIV-1 replication in CD4+ lymphocytes by tumor necrosis factor (TNF) and/or prevent damage to or death of CD4+ cells as a consequence of HIV-1 infection. Without wishing to be bound by any particular theory of HIV-1 replication or HIV-1 pathogenesis, it is believed that administration of a salophene-based metallic complex inhibits and/or slows the development of HIV-1 related pathology and/or reduces the rate of decline of the CD4+ lymphocyte population in HIV-infected individuals. The salophene-based metallic complexes also inhibit pathology resulting from excessive or inappropriate levels of TNF, both in AIDS and in other conditions (e.g., septic shock). Frequently, a dosage of about 50 to 5000 mg will be administered to a patient with HIV and/or with excessive or inappropriate levels of TNF, either in single or multiple doses, to reduce or retard the development of pathology and clinical symptoms. Salophene-based metallic complex are administered therapeutically to treat viral diseases other than HIV.

In general for treatment of neoplastic diseases, a suitable effective dose of salophene-based metallic complex will be in the range of 0.01 to 1000 milligram (mg) per kilogram (kg) of body weight of recipient per day, preferably in the range of 1 to 100 mg per kg of body weight per day. The desired dosage is preferably presented in one, two, three, four or more subdoses administered at appropriate intervals throughout the day. These subdoses can be administered as unit dosage forms, for example, containing 5 to 10,000 mg, preferably 10 to 1000 mg of active ingredient per unit dosage form.

EXAMPLE 1

Ovarian Cancer

A 66 year old female presents with stage III ovarian cancer. She is treated with 3 mg per kg of body weight with a metal-losalophene for 10 days. The tumor burden by imaging is significantly reduced.

The composition used in these therapies can be in a variety of forms. These include, for example, solid, semi-solid and liquid dosage forms, such as tablets, pills, powders, liquid solutions or suspensions, liposome preparations, injectable and infusible solutions. The preferred form depends on the intended mode of administration and therapeutic application. Typically, a sterile solution of a salophene-based metallic complex in an aqueous solvent (e.g., saline) will be administered intravenously. The compositions also preferably include conventional pharmaceutically acceptable carriers and adjuvants which are known to those of skill in the art. See, e.g., *Remington: The Science and Practice of Pharmacy*, Ed. Randy Hendrickson, Lippincott, Williams & Wilkins, 21$^{st}$ Edition (2005). Generally, administration will be by oral or parenteral (including subcutaneous, intramuscular, intravenous, and intradermal) routes, or by topical application or infusion into a body cavity, or as a bathing solution for tissues during surgery.

It should, of course, be understood that the methods of this invention can be used in combination with other antioxidant agents that have SOD (superoxide dismutase) activity, catalase activity, glutathione peroxidase (GSH-Px)) activity, or are free radical scavengers or inhibitors of free radical formation. It is possible to administer the active ingredient of this invention as a single active pharmaceutical agent, and also as part of a pharmaceutical formulation. The pharmaceutically acceptable formulations of the present invention comprise at least one compound of this invention in a therapeutically or pharmaceutically effective dose together with, optionally, one or more pharmaceutically or therapeutically acceptable carriers and optionally other therapeutic ingredients. Carriers include inert, non-toxic solids (e.g., mannitol, talc) and buffered saline. Various considerations are described in, for example, *Goodman and Gilman's: The Pharmacological Bases of Therapeutics*, Eds. Laurence Brunton, John Lazo, Keith Parker 11th Ed., Pergamon Press (2005); and Remington's supra, each of which is hereby incorporated herein by reference. Methods for administration are discussed therein, e.g., for oral, intravenous, intraperitoneal, or intramuscular administration, and others. Pharmaceutically acceptable carriers will include water, saline, buffers, and other compounds described in a number of sources including the *Merck Index*, Merck & Co., Rahway, N.J., incorporated herein by reference. As used herein, the term "pharmaceutically acceptable carrier" encompasses any of the standard pharmaceutical carriers such as sterile solutions, tablets, coated tablets, and capsules. Typically such carriers contain excipients such as starch, milk, sugar, certain types of clay, gelatin, stearic acids or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods. Depending on the intended mode of administration and the intended use, the compositions may be in the form of solid, semi-solid, or liquid dosage forms, such, for example, as powders, granules, crystals, liquids, suspensions, liposomes, pastes, cremes, salves, etc., and may be in unit-dosage forms suitable for administration of relatively precise dosages. For semi-solid compositions, as would be appropriate for pastes and creams intended for topical administration, the salophene-based metal complexes can be provided separately or may be compounded with conventional nontoxic carriers such as, for example, aloe vera gel, squalane, glycerol stearate, polyethylene glycol, cetyl alcohol, stearic acid, and propylene glycol, among others. Such compositions may contain about 0.005-100% active ingredient, more preferably about 0.5-25%. The concentration of the salophene-metal complexes in these formulations can vary widely, and will be selected primarily by intended use, viscosities, etc., in accordance with the particular mode of administration selected. The composition or formulation to be administered will, in any event, contain a quantity of the salophene-based metallic complex sufficient to achieve the desired therapeutic or prophylactic effect in the subject being treated. Typical compositions include lotions containing water and/or alcohols and emollients such as hydrocarbon oils and waxes, silicone oils, vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophillic colloids. Such compositions are referred to herein as dermatologically acceptable carriers.

The pharmaceutical compositions will be administered by parenteral or oral administration for prophylactic and/or therapeutic treatment. The pharmaceutical compositions can be administered in a variety of unit dosage forms depending upon the method of administration. For example, unit dosage forms suitable for oral administration include powder, tablets, pills, capsules, trochees, and dragees.

The pharmaceutical compositions will often be administered intravenously. Thus, this invention provides compositions for intravenous administration which comprise a solution of the compound dissolved or suspended in an acceptable carrier, preferably an aqueous carrier. A variety of aqueous carriers can be used, e.g., water, buffered water, 0.4% saline, and the like. Often, the salophene-based metallic complex is dissolved in an organic solvent (e.g., dimethylsulfoxide) and either applied directly or diluted into an aqueous solvent. Typically, salophene-based metallic complexes that are relatively lipophilic (e.g., C9, C12 and greater than C12) are dissolved in an organic solvent such as DMSO and, if desired, subsequently diluted into a more polar solvent, such as water. These compositions will sometimes be sterilized by conventional, well known sterilization techniques, or can preferably be sterile filtered. The resulting aqueous solutions can be packaged for use as is, or lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.001-95% of active ingredient, preferably about 20%.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective amount or dose." Amounts effective for this use will depend on the severity of the disease and the weight and general state of the patient.

In prophylactic applications, compositions containing the compounds of the invention are administered to a patient susceptible to or otherwise at risk of a particular disease. Such an amount is defined to be a "prophylactically effective amount or dose." In this use, the precise amounts again depend on the patient's state of health and weight.

For solid compositions, conventional non-toxic solid excipients include, for example, pharmaceutical grades of mannitol, lactose, starch, magnesium stearate, talcum, celluloses, glucose, sucrose, magnesium carbonate, and the like may be used. The active compound as defined above may be formulated as suppositories using, for example, triglycerides, for example, any pharmaceutically acceptable Hard Fat NF bases (e.g., WITEPSOL.RTM™, Condea Vista Company, Cranford, N.J.), as the carrier. Liquid pharmaceutically administerable compositions can, for example, be prepared by dissolving, dispersing, etc. an active compound as defined above and optional pharmaceutical adjuvants in a excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington: The Science and Practice of Pharmacy, Ed. Randy Hendrickson, Lippincott, Williams & Wilkins, 21$^{st}$ Edition (2005). The composition or formulation to be administered will, in any event, contain an effective amount of the active compound(s).

For oral administration, a pharmaceutically acceptable non-toxic composition is formed by the incorporation of any of the normally employed excipients, such as, for example pharmaceutical grades of mannitol, lactose, starch, magnesium stearate, talcum, celluloses, glucose, sucrose, magnesium, carbonate, and the like. Such compositions take the form of solutions, suspensions, tablets, capsules, powders, sustained release formulations and the like. Such compositions may contain 0.01-95% active ingredient, preferably 1-70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. Nos. 5,629,008, 5,851,547, 6,183,461, and 3,710,795, which are incorporated herein by reference. Salophene-based metal complexes may be administered by transdermal patch (e.g., iontophoretic transfer) for local or systemic application.

Once detectable improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms or as a prophylactic measure to prevent disease symptom recurrence. In particular embodiments extended release formulations are contemplated.

Salophene-based metallic complex are also be added to extravasated blood for transfusion to inhibit oxyradical damage to the blood cells and components during storage; similarly, salophene-based metal complexes can also reduce oxyradical damage to blood cells in vivo.

Salophene-based metallic complex could also be added to rinse or storage solutions for organs and tissues, such as for organ transplantation or for surgical rinses. For example, excised organs are often placed in a preservation solution prior to transplant into a recipient. Inclusion of at least one species of salophene-based metallic complex in a preservation solution, usually at a concentration of about 0.01 mM to 10 mM, is desirable for reducing damage due to ischemia during storage and reperfusion injury following reimplantation in the recipient. Various solutions described in the art are suitable for the inclusion of a salophene-based metallic complex, including but not limited to those described in U.S. Pat. No. 5,145,771; Beyersdorf (1990) Chem. Abst. 113: 84849w; U.S. Pat. Nos. 4,879,283; 4,873,230; and 4,798,824, incorporated herein by reference.

Typically the salophene-based metallic complex is present in the rinse or storage solution at a concentration of about 10 microM to about 10 mM, and most usually is present at 1 mM. For example, but not to limit the invention, a suitable rinse solution comprises Ringer's solution (102 mM NaCl, 4 mM KCl, 3 mM $CaCl_2$, 28 mM sodium lactate, pH 7.0) or Ringer's solution with 0.1 mM adenosine, and the salophen-based metallic complex at a final concentration of 1 mM. The rinse solution can further comprise additional antioxidants (e.g., glutathione, allopurinol). Preservation or rinse solutions containing an salophene-based metal complex can be used to provide enhanced storage or irrigation of organs (e.g., kidney, liver, pancreas, lung, fetal neural tissue, heart, vascular grafts, bone, ligament, tendon, skin) which is believed to enhance the viability of the tissue and increase resistance to oxidative damage (e.g., as a consequence of ischemia/reperfusion).

The invention claimed is:
1. A compound of formula

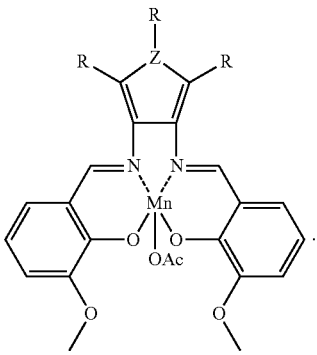

Z is selected from the group consisting of C, N, O or S; and,
R is selected from the group consisting of H, amino, hydroxyl, halogens, alkyl, aryl, heteroaryl, arylalkyl, acetyl, carbamates, urea, or thiourea,
alkyl, alkenyl, alkynyl, aryl, heteroaryl, arylalkyl, heteroarylalkyl, OH, COOH, CHO, halide, $NO_2$, or $NH_2$, or said substituent further combined with at least one substituent selected from the group consisting of amide, urea, thiourea, CN, bicyclic amine, or bicyclicdiamine.

2. A compound of formula

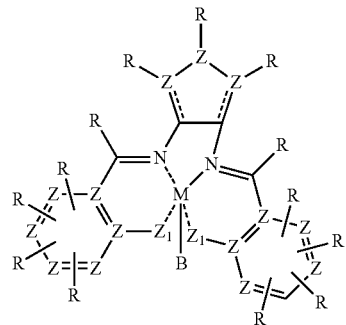

B is selected from ligands such as halides, acetate, oxalates, succinate, fumarates, or tartarates;

Z is selected from the group consisting of C, N, O or S;

R is selected from the group consisting of H, amino, hydroxyl, halogens, alkyl, aryl, heteroaryl, arylalkyl, acetyl, carbamates, urea, or thiourea, alkyl, alkenyl, alkynyl, aryl, heteroaryl, arylalkyl, heteroarylalkyl, OH, COOH, CHO, halide, $NO_2$, or $NH_2$, or said substituent further combined with at least one substituent selected from the group consisting of amide, urea, thiourea, CN, bicyclic amine, or bicyclicdiamine;

M is Fe;

$Z_1$ is selected from the group consisting of O, N or S.

3. A compound of formula

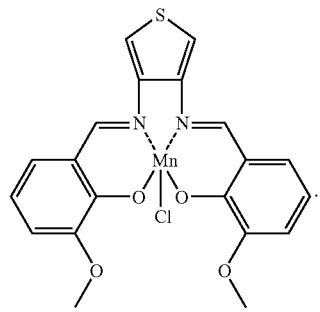

4. A method of treating ovarian cancer by administering to subject a therapeutically effective dose of a compound of claim 1, 2, or 3.

* * * * *

UNITED STATES PATENT AND TRADEMARK OFFICE
CERTIFICATE OF CORRECTION

| | | |
|---|---|---|
| PATENT NO. | : 8,252,780 B2 | Page 1 of 1 |
| APPLICATION NO. | : 12/516878 | |
| DATED | : August 28, 2012 | |
| INVENTOR(S) | : Laurent Brard et al. | |

It is certified that error appears in the above-identified patent and that said Letters Patent is hereby corrected as shown below:

Column 1, line 4, insert the following:

--Statement Regarding Federally Sponsored Research or Development

This invention was made with Government support under Grant No. 1 R01 GM61915-01A1 awarded by the National Institute of Health (NIH). The Government has certain rights in the invention.--

Signed and Sealed this
Fourth Day of December, 2012

David J. Kappos
*Director of the United States Patent and Trademark Office*

UNITED STATES PATENT AND TRADEMARK OFFICE
CERTIFICATE OF CORRECTION

PATENT NO. : 8,252,780 B2
APPLICATION NO. : 12/516878
DATED : August 28, 2012
INVENTOR(S) : Laurent Brard et al.

Page 1 of 1

It is certified that error appears in the above-identified patent and that said Letters Patent is hereby corrected as shown below:

In the Specification

Column 1, Line 4, Statement Regarding Federally Sponsored Research or Development:
Delete the following:
"This invention was made with Government support under Grant No. 1 RO1 GM61915 01A1 awarded by the National Institute of Health (NIH). The Government has certain rights in the invention."
And insert therefor:
-- This invention was made with government support under GM61915 awarded by the National Institutes of Health. The government has certain rights in the invention. --

This certificate supersedes the Certificate of Correction issued December 4, 2012.

Signed and Sealed this
Twenty-fourth Day of March, 2020

Andrei Iancu
*Director of the United States Patent and Trademark Office*

UNITED STATES PATENT AND TRADEMARK OFFICE
CERTIFICATE OF CORRECTION

Page 1 of 1

PATENT NO. : 8,252,780 B2
APPLICATION NO. : 12/516878
DATED : August 28, 2012
INVENTOR(S) : Laurent Brard et al.

It is certified that error appears in the above-identified patent and that said Letters Patent is hereby corrected as shown below:

In the Specification

Column 1, Line 4, Statement Regarding Federally Sponsored Research or Development delete the following:
"This invention was made with government support under GM61915 awarded by the National Institutes of Health. The government has certain rights in the invention."

And insert therefor:
-- This invention was made with government support under EB002044 awarded by the National Institutes of Health. The government has certain rights in the invention. --

Signed and Sealed this
Ninth Day of June, 2020

Andrei Iancu
*Director of the United States Patent and Trademark Office*